(12) United States Patent
Eklin et al.

(10) Patent No.: US 6,934,021 B2
(45) Date of Patent: Aug. 23, 2005

(54) METHOD AND ARRANGEMENT FOR APPLYING OPTICAL EMISSION SPECTROSCOPY TO THE DETECTION OF THE 193 NM SPECTRAL LINE OF CARBON

(75) Inventors: Tero Eklin, Espoo (FI); Mikko Krapu, Helsinki (FI)

(73) Assignee: Oxford Instruments Analytical Oy, Espoo (FI)

( * ) Notice: Subject to any disclaimer, the term of this patent is extended or adjusted under 35 U.S.C. 154(b) by 92 days.

(21) Appl. No.: 10/650,014

(22) Filed: Aug. 27, 2003

(65) Prior Publication Data

US 2004/0160602 A1 Aug. 19, 2004

Related U.S. Application Data

(63) Continuation-in-part of application No. 10/609,817, filed on Jun. 30, 2003.

(30) Foreign Application Priority Data

Sep. 18, 2002 (FI) .............................................. 20021666

(51) Int. Cl.⁷ ............................. G01J 3/30; G01N 21/67
(52) U.S. Cl. ...................................................... 356/313
(58) Field of Search ........................................ 356/313

(56) References Cited

U.S. PATENT DOCUMENTS 4,411,524 A 10/1983 Kremer et al.
4,641,968 A 2/1987 Grandy
5,141,314 A 8/1992 Belmore et al.

FOREIGN PATENT DOCUMENTS

GB 2095824 A 10/1982

OTHER PUBLICATIONS

European Search Report communicated Jan. 13, 2005, re EP 03 39 6085 (counterpart of this US application).

Primary Examiner—F. L. Evans
(74) Attorney, Agent, or Firm—Wood, Phillips, Katz, Clark & Mortimer

(57) ABSTRACT

A measurement device and method are provided for OES measurements in air. An arc electrode (201, 501) has a certain thickness and a pointed end having a certain grinding angle. Holding means (202, 502) hold the arc electrode (201, 501) at a certain distance from the material to be measured. A voltage and current supply (203) generates and maintains a voltage between the arc electrode and the material to be measured and supplies current through the arc. Focusing and detection optics (205, 206, 402, 403, 404, 405, 406, 407, 408, 505, 506, 509, 604) collect and detect optical radiation. The thickness of the arc electrode (201, 501) is between 3 and 10 mm and the grinding angle is between 50 and 130 degrees. The arc distance is between 0.5 and 3 mm. An ignition spark voltage is between 5 and 20 kV, an arc voltage between 20 and 160 V and an arc current between 1 and 10 A. The focusing and detection optics (205, 206, 402, 403, 404, 405, 406, 407, 408, 505, 506, 509, 604) collect and detect at least optical radiation on a wavelength of 193 nm.

16 Claims, 4 Drawing Sheets

METHOD AND ARRANGEMENT FOR APPLYING OPTICAL EMISSION SPECTROSCOPY TO THE DETECTION OF THE 193 NM SPECTRAL LINE OF CARBON

CROSS-REFERENCE TO RELATED APPLICATION

This application is a continuation-in-part of U.S. patent application Ser. No. 10/609,817, which was filed on Jun. 30, 2003, and the disclosure of which is incorporated herein by reference.

TECHNICAL FIELD

The invention concerns generally the technology of measurement methods and devices that employ optical emission spectroscopy. Especially the invention concerns finding a solution that overcomes the known problems of detecting the 193 nm spectral line of carbon.

BACKGROUND OF THE INVENTION

Optical emission spectroscopy (or OES for short) means in general a measurement method in which atoms and molecules of a target material are provided with a sufficient stimulus that causes said particles to be excited into certain excited states, the spontaneous relaxation of which causes detectable emission in the optical wavelengths of the spectrum of electromagnetic radiation.

FIG. 1 illustrates an OES arrangement that is known from a prior art patent publication DE 38 40 106. A measuring head or test probe 101 is brought into contact with an electrically conductive target material 102. A high voltage is applied between the target material 102 and an electrode 103 within the measuring head, thus causing an electric arc to be ignited therebetween. The energy involved in the electric discharge causes atoms and molecules of the target material 102 to be evaporized into the chamber-like space 104 that surrounds the lower end of the electrode 103, where the excited evaporated particles constitute a plasma. Spontaneous relaxation of the excited states of the particles cause electromagnetic radiation in the optical range to be emitted. A part of the emitted radiation travels through a collimator 105 and hits a deflecting mirror 106, which directs the radiation through a slit 107 onto a wavelength-dispersive focusing mirror 108 and further to a detector 109. Knowing the characteristics of the optical system it is possible to deduce the wavelength of a certain part of the incident radiation by noting the spot at which it hit the detector 109.

A major area of application for OES measurements is in the field of metallurgy, where OES analyzers are frequently used both in laboratory and on-site conditions for purposes like sorting, material control and process management. Carbon is an important element in this respect because of its alloying properties, and in many OES measurements it would be especially advantageous if carbon could be measured reliably. The best analytical spectral line of carbon corresponds to emitted radiation at a wavelength of 193.090 nm in vacuum; this spectral line is commonly referred to as the "193 nm line" of carbon. However, it has been commonly regarded as impossible to measure it with an OES arrangement where the arc chamber is not isolated from the ambient air. Optical emission spectrometers for measuring the 193 nm line of carbon are commercially available, but they have the common feature that they require the test probe to be flushed with an inert gaseous medium, usually argon. Additionally there have been problems with lightguides: the transmissivity of known optical fiber lightguides tends to drop dramatically at wavelengths below about 200 nm.

The problems of detecting the 193 nm line of carbon in air have been addressed for example on page 310 of K. Slickers: "Automatic-Emission-Spectroscopy", Bruhlsche Universitetsdruckerei, Giessen, Germany, $2^{nd}$ edition, 1993, which is widely regarded as the most authoritative monographic volume in this technological field. On the same page the author suggests that measurements with argon-flushed test probes are the most likely way to successive on-site detection.

The relative ease of measuring the 193 nm line of carbon with an argon-flushed test probe has resulted in a situation where all commercially available on-site OES measurement devices use argon flushing. Although it enables the measurement to succeed, the requirement for carrying a pressurized container of argon around is a major disadvantage that limits the usability of OES arrangements.

An alternative approach to the OES measurement of carbon is to use the molecular, so-called CN emission bands, of which the one having a wavelength of 387.1 nm is most readily available. Such an approach has been described for example in N. N. Sorokina and P. A. Kondrat'ev: "A Spectral Method for Determining Carbon by Cyanogen Bands" (russ.), Zavodskaja Lab. 31 (1964), pp. 1344–1345. The CN emission bands do not facilitate obtaining as exact and unequivocal measurement results as would the atomic emission line of 193 nm.

SUMMARY OF THE INVENTION

It is an objective of the present invention to provide a method and an arrangement for measuring the 193 nm spectral line of carbon without having to flush the test probe with an inert gaseous medium. It is an additional objective of the invention to provide a method and an arrangement for measuring the 193 nm line of carbon through air. A yet further objective of the invention is that the method and arrangement according to the invention are applicable to on-site use with portable measurement devices.

The objectives of the invention are achieved by selecting the measurement parameters in a suitable way so that the temperature within the measurement area can be kept low enough for the 193 nm line of carbon to become available for detection. Especially the arc electrode is made relatively thick and blunt. Arc current, arc voltage and ignition voltage are also kept relatively low, so that there is obtained a relatively long period of time during which carbon atoms are excited effectively but oxidation and carbon molecule build-up can be kept low enough.

A measurement device according to the invention is characterized by the features that are recited in the appended independent patent claim directed to a measurement device.

The invention applies also a measurement method, which is characterized by the features that are recited in the appended independent patent claim directed to a measurement method.

Various embodiments of the invention are introduced in the depending claims.

In the research that led to the present invention it was found that the relaxation of the atomic excited state of carbon, associated with the emission at the 193 nm wavelength, and the masking reactions like oxidation and molecule build-up are actually competing processes. A most important observation was that since the masking processes are chemical by nature, their reaction rate is an exponential function of temperature. On the contrary, the relaxation of an excited state in a carbon atom is a phenomenon related to quantum physics and does not depend on temperature to any essential extent. Thus, by keeping the temperature of the arc low enough, it is possible to suppress the effect of the masking processes, so that a sufficient number of excited carbon atoms undergo relaxation and emit radiation at the wavelength of 193 nm with a measurable intensity.

There are several process parameters the values of which affect the temperature of the arc and consequently the chances of detecting the 193 nm line of carbon. Firstly, the electrode that is used for producing the arc must not be thin and sharp, but relatively thick and blunt instead. This helps to keep the arc from being concentrated into a very small spatial area, which is synonymous to saying that the thick electrode helps to keep the spatial current density low. The current through the arc is also limited to achieve the same purpose, low current density. Other parameters that must be suitably selected are the distance between the electrode and the material to be measured, the ignition spark voltage used to ignite the arc, as well as the arc voltage used to maintain the arc during the measurement.

For a DC arc the following useful ranges for the above-mentioned process parameters have been found:

arc current 1–10 A arc voltage 20–160 V ignition spark voltage 5–20 kV thickness of an Ag or Cu electrode 3–10 mm tip angle of the electrode 50–130 degrees distance between electrode and measured material 0.5–3 mm.

With these parameter values it has been observed that a total measurement time between 0.5 and 5 seconds yields good results in detecting the 193 nm line of carbon.

As an alternative to a simple DC arc it is also possible to use a parameterized pulsed DC arc with a pulse frequency between 2 and 500 Hz.

BRIEF DESCRIPTION OF DRAWINGS

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

Figure 2:
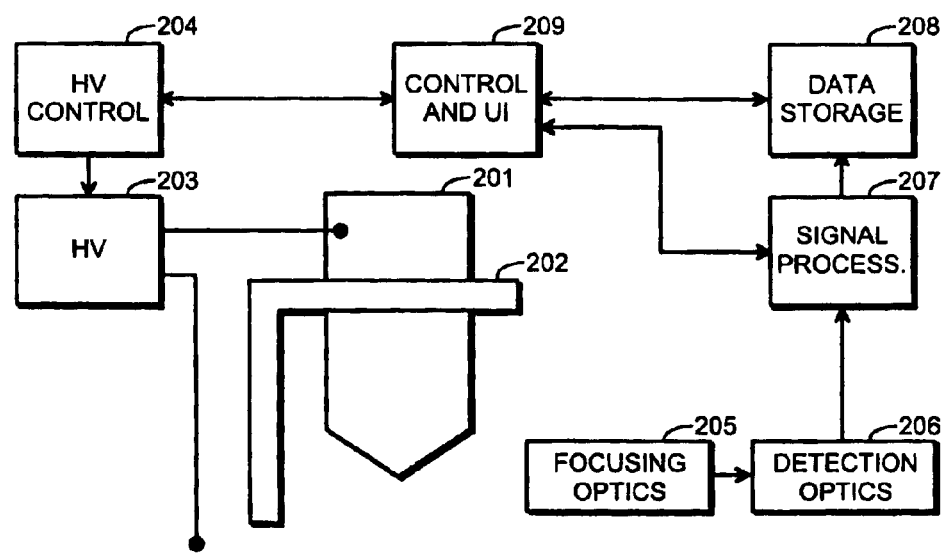
FIG. 2 illustrates schematically certain components of an OES measurement arrangement according to the invention.

FIG. 2 illustrates schematically those components of an OES measurement arrangement for which important requirements are placed in accordance with the present invention. An electrode 201 must be present, acting as one end of the electric arc to be ignited between the measurement arrangement and a material to be examined. Some kind of a holder 202 is needed for standardising the mechanical relationship between the electrode 201 and a material surface during a measurement. A high voltage source 203 must be present for setting up the ignition voltage between the electrode 201 and a material to be measured, as well as sustaining the arc during the measurement. A high voltage control unit 204 controls the operation of the high voltage source 203. Located at least partly in the immediate vicinity of the arcing area there must be certain focusing optics 205, the task of which is to collect electromagnetic radiation emitted by the particles of the plasma in the arc. Optically coupled to the last-mentioned, detection optics 206 are needed for separating collected wavelengths from each other and detecting the intensity associated with each wavelength.

An electronic signal processing unit 207 must be present in order to collect, amplify and process the signals produced in the detection optics 206 appropriately so that they can be stored in a data storage unit 208. A central part of the apparatus is a control and user interface unit 209, which is coupled to control the high voltage control unit 204, the signal processing unit 207 and the data storage 208 according to commands received from a user. The control and user interface unit 209 additionally provides output for the user, describing the state of the system as well as the obtained measurement results.

The requirements, which the present invention places to the components shown in FIG. 2, are as follows. The electrode 201 must be thick and blunt enough to enable the generation and sustaining of a spatially large arc; for the same reason the holder 202 must be arranged to keep the separation distance between the tip of the electrode and the material to be measured small enough. What is "enough" in this respect is considered in more detail later with reference to FIG. 3. The combination of a high voltage source 203 and a high voltage control unit 204 must be arranged to produce a relatively low arc current as well as a relatively slow arc ignition process. The optical transmissivity of the focusing optics 205 must be as good as possible at the wavelength of 193 nm, and the detection optics 206 must be arranged to direct radiation of this wavelength appropriately to a detector and to produce a good, sharp signal that reveals the intensity of the detected radiation at 193 nm. The signal processing and data storage units 207 and 208 must also be optimised so that results that show the amount of detected radiation at 193 nm can be documented and stored.

Figure 3:
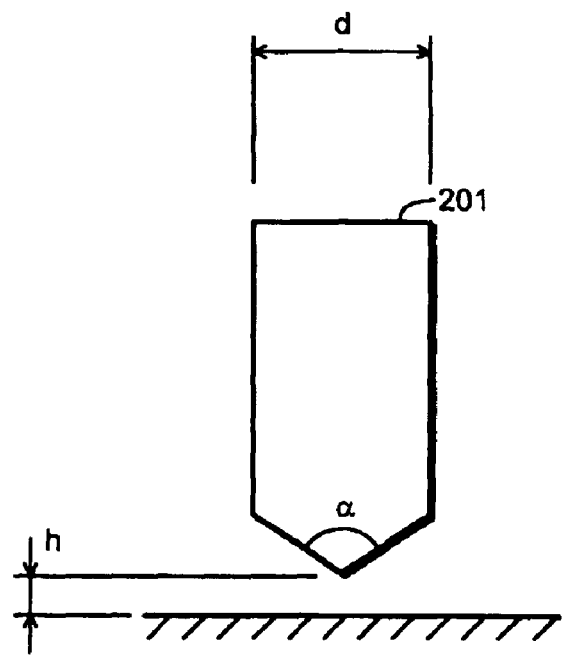
FIG. 3 illustrates certain dimensioning aspects related to the arc electrode.

FIG. 3 provides some explanation to the question of exactly how should the arcing area be designed mechanically. The electrode 201 is typically made of silver or copper; in any case its material must be as good an electric conductor as possible. It is also advantageous if the material of the electrode is free from impurities and has a high melting point, but these are all requirements that apply to all OES arc electrodes. If the apparatus is to be used for measuring carbon, the material of the electrode should be as free from carbon as possible. According to the present invention the thickness d of at least part of the electrode is between 2 and 10 mm, the tip angle or grinding angle α of the electrode is between 40 and 130 degrees, and the separation h between the tip of the electrode and the material to be measured is between 0.5 and 3 mm. It has been found that by keeping said dimensions within these limits it is possible to keep the spatial current density in an arc low enough so that enough excitation of atomic carbon occurs, but the masking effects of oxidization and molecule build-up can be kept low.

Figure 4:
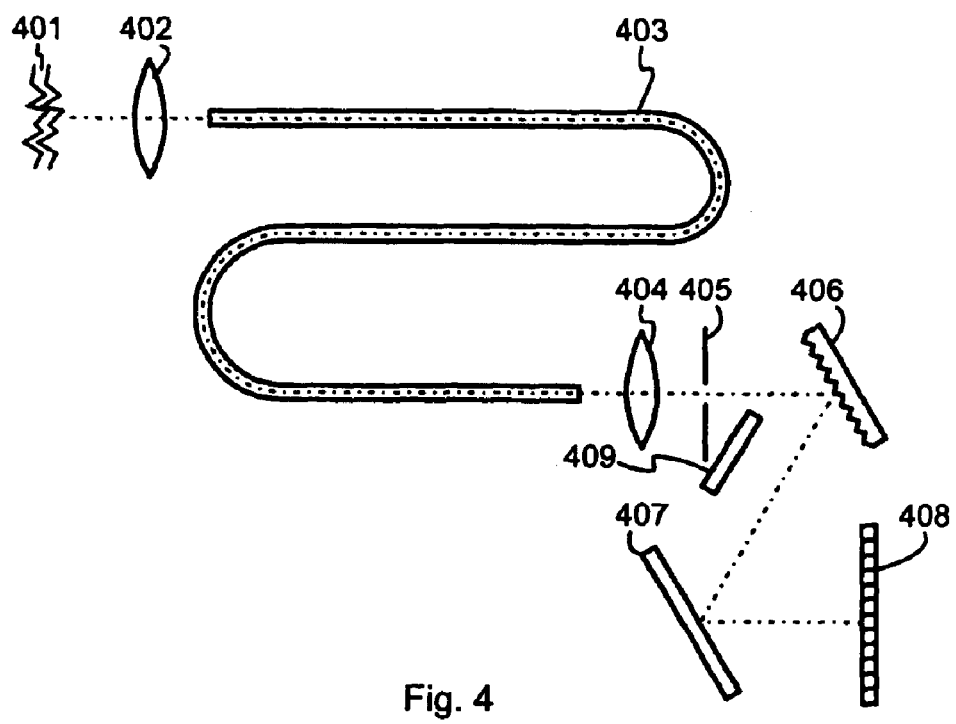
FIG. 4 illustrates schematically certain optical components in a measurement device according to the invention.

The most important feature of the focusing optics, in respect of the present invention, is its optimized transmissivity on 193 nm. With the optical fibre materials known at the priority date of this patent application, fibre lengths of several meters can be ruled out, but optical fibres with the length of less than 60 cm can be used. FIG. 4 illustrates schematically an exemplary combination of focusing and detection optics. Closest to the arc 401 there is a focusing lens 402, which directs a part of the emitted optical radiation into an optical fibre 403. At the other end of the fibre 403 there is a collimator 404 and a slit 405, which together produce a highly collimated narrow optical beam that hits a grating 406. The purpose of the grating 406 is to cause wavelength-dependent spatial dispersion so that when optical radiation continues from the grating 406 onto a reflecting mirror 407 and further to a linear detector 408, radiation components of different wavelengths hit different positions in the detector. One purpose of the mirror 407 is to make the optical path longer; if the resolution is not severely affected, the detector could as well be placed immediately after the grating on the optical path. Additionally using a mirror to "fold" the optical path allows the mechanics of a measurement head to be designed in an advantageous way, because a long linear dimension in one direction is not needed. In order to enhance detection reliability it may prove to be useful to place a light limiter 409 between the slit 405 and the detector 408, so that any scattered stray radiation from the slit is kept from finding its way to the detector.

Figure 1:
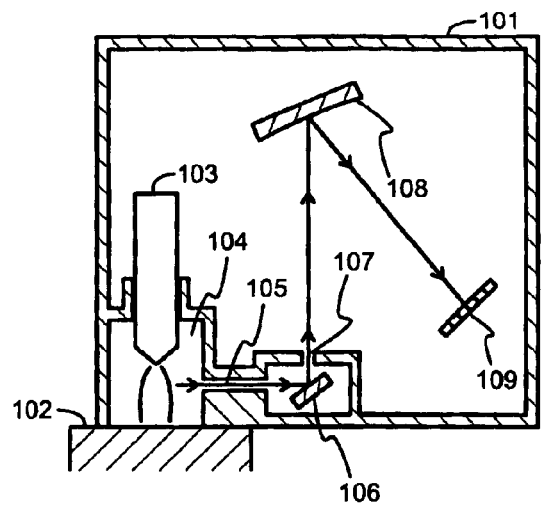
FIG. 1 illustrates a known OES measurement arrangement

The exact implementation of the focusing and detecting optics is not of primary importance to the invention, as long as it fulfils its task of effectively and reliably detecting the 193 nm line of carbon. The exemplary arrangement of FIG. 4 could be modified in various ways. For example an optical fibre is not needed at all, if the optical arrangement is made to resemble more the known arrangement of FIG. 1 or any of its alternatives disclosed in DE 38 40 106. A linear semiconductor detector could be replaced with a two-dimensional matrix detector or a collection of adjacent photodiodes and photomultiplier tubes. Semiconductor detectors can be based on any of the known technologies like PDA (Photo-Diode Array), CCD (Charge-Coupled Device), CMOS (Complementary Metal Oxide Semiconductor) or CID (Charge Injection Device).

Naturally the invention does not preclude using argon or some other inert gaseous medium to flush the arcing area and the optical path; however, there are many advantages in not using any flushing. It is not necessary to hone and polish a large area of the material to be measured, because the arcing area does not need to be sealed against ambient air—this helps to shorten the overall time needed for measuring. The block of material to be measured does not need to have a regular form, at least not to the extent required in argon-flushed measurements. Not consuming some relatively expensive flushing gas naturally helps also to reduce operating costs.

Figure 5:
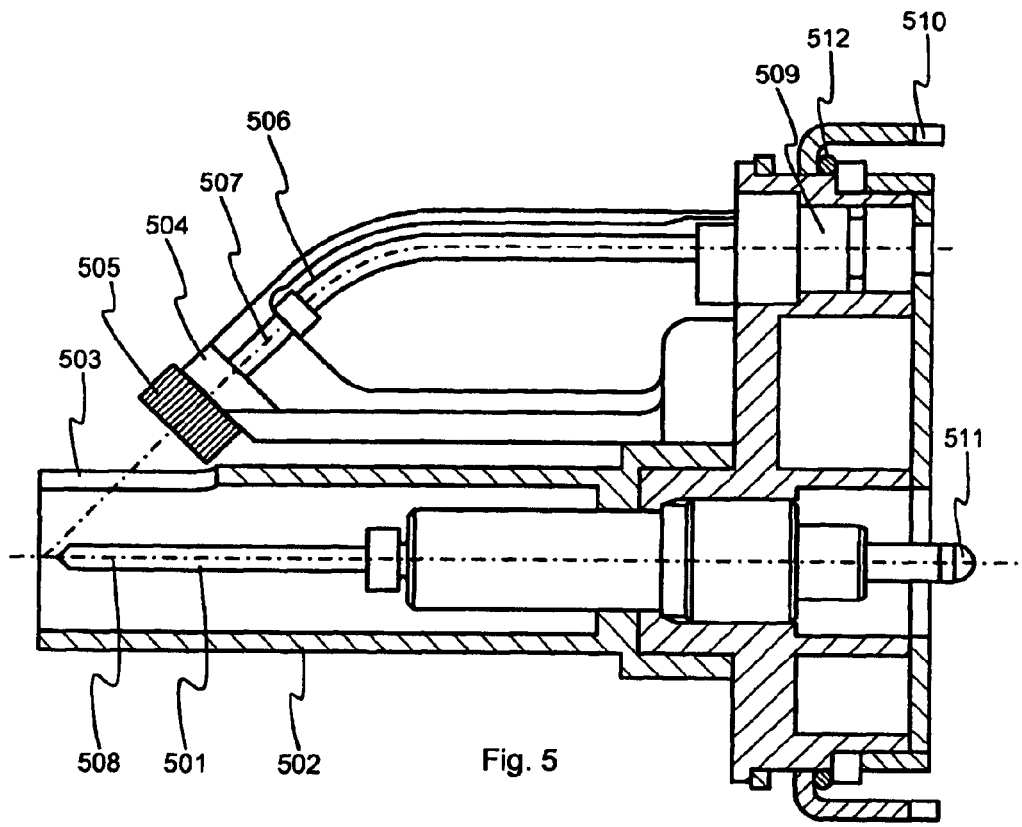
FIG. 5 illustrates the mechanical structure of a measurement head according to the invention.

FIG. 5 illustrates, in a partial cross section, the mechanical structure of a measurement head according to an embodiment of the invention. The arc electrode 501 is located coaxially in a shielding tube 502, one end of which (the left-hand end in FIG. 5) is open. A part of the wall of the shielding tube 502 has been cut out near the open end, so that the edges 503 of the cut-out portion define a window through which the arcing area is visible. A lens and fibre holder 504 is located along one side of the shielding tube 502. Attached to the lens and fibre holder 504 there are a lens 505 and an optical fibre 506. The optical axis 507 of the lens 505 is directed towards the arcing area so that it intersects the common central axis 508 of the arc electrode 501 and the shielding tube 502 at a point that is between the tip of the electrode and the level at which the surface of the material to be measured will appear. Assuming that the surface of the material to be measured is flat, said level coincides with the level of the edges of the shielding tube 502 at its open end.

One end of the optical fibre 506 is located on the optical axis 507 of the lens 505, so that optical radiation that comes from the arcing area and hits the lens 505 is directed into the optical fibre 506. The central axis of the optical fibre 506 thus extends the optical axis of the focusing optics arrangement from the lens 505 onwards. The length of the optical fibre 506 is in this embodiment of the invention about 65 mm. At the other end of the optical fibre 506 there is a lens or a corresponding collimator arrangement 509 that collects the optical radiation that exits the optical fibre 506 into a well-collimated beam. The measurement head of FIG. 5 is meant to be attached to another entity that contains the detection optics, which means that in such another entity there must be a radiation input section (typically a slit), the optical axis of which coincides with the collimated beam formed in the collimator arrangement 509.

A part of the measurement head (in FIG. 5 is the rightmost portion thereof) contains mechanical attachment means 510 and high voltage connection means 511 for connecting the measurement head to a detection optics unit and for delivering the arc voltage and current to the arc electrode. For certain purposes it may be useful if the mechanical attachment means 510 contain or can be equipped with sealing surfaces and gaskets 512 for making the attachment to the detection optics unit gastight.

Figure 6:
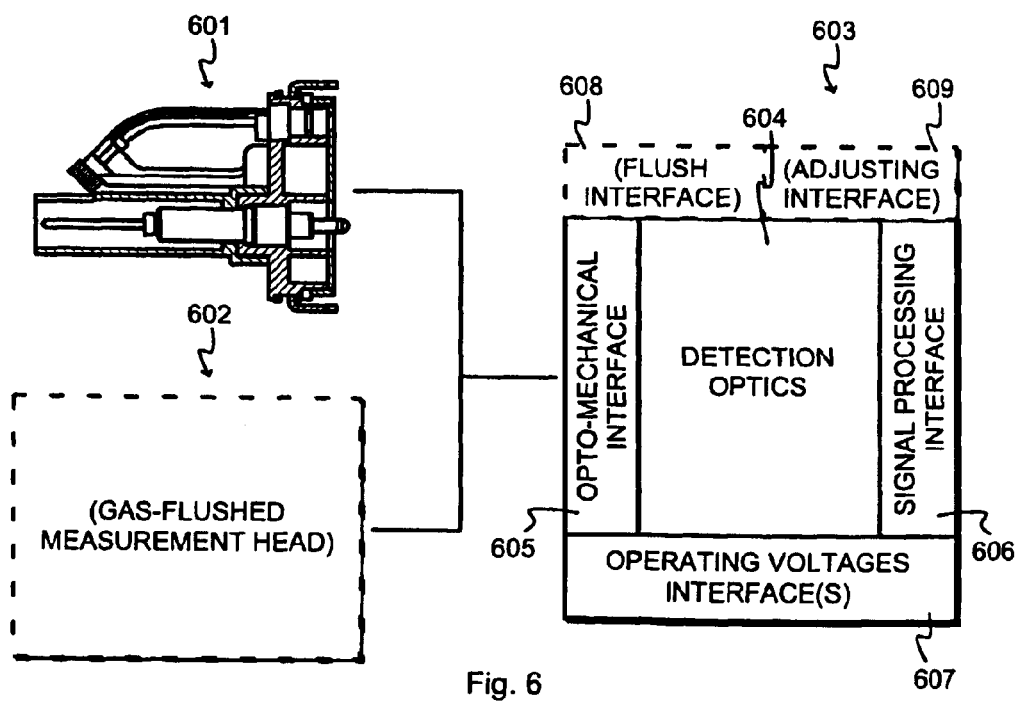
FIG. 6 illustrates the principle of interchangeable measurement heads according to the invention and FIG. 7 illustrates certain voltage and current characteristics in a method according to the invention.

FIG. 6 illustrates an advantageous use of a measurement head 601 according to the embodiment of FIG. 5. In this arrangement the measurement head 601, which is meant for measuring the 193 nm line of carbon in air, is interchangeable with a gas-flushed measurement head 602 which otherwise represents prior art technology. Only a single detection optics unit 603 is needed. The last-mentioned contains the actual detection optics 604 as well as an opto-mechanical interface 605 that has been designed to match the mechanical attachment means in the measurement heads and to accept the optical radiation that comes as a collimated beam from the measurement head connected thereto. For delivering further the signals that represent detected radiation the detection optics unit 603 contains a signal processing interface 606. Additionally it contains one or more operating voltages interfaces 607 for introducing the operating voltages for the detector arrangement into the detection optics unit 603; typically it is also advantageous to deliver the arc voltage and current to the measurement head through the detection optics unit 603, in which case the operating voltages interfaces 607 also contain the required high voltage inputs and outputs.

Considering the facts that air attenuates heavily certain important wavelengts and that also in the detection optics 604 the collected radiation passes through significant passages of free space, it may prove useful to flush the detection optics 604 with a more suitable gaseous medium than air. For this purpose the detection optics unit 603 may contain a flush interface 608 through which the flushing medium can be provided. Additionally taking into account that the open-to-ambient-air measurement head 601 does not require flushing (although not precluding it either) but the gas-flushed measurement head 602 positively does, it is advantageous to design the opto-mechanical interface 605 to include a valve, through the setting of which it can be selected, whether gas supplied to the flush interface 608 is allowed to flow also to the measurement head. The sealing surfaces and gaskets mentioned earlier in assocation with FIG. 5 are useful especially if the detection optics 604 are gas-flushed but arcing will be performed through air, because a gastight interface between the detection optics unit 603 and the measurement head 601 prevents valuable flushing gas from leaking out from the detection optics unit 603.

Changing the measurement head or even using a single measurement head for different kinds of measurements may require certain adjustments to be made in the detection optics unit 603: for example the mutual location and/or direction of the optical elements may require changing if a subsequent measurement will concern different wavelengths. Therefore it is advisable to include some kind of adjustment possibility into the detection optics unit 603. In FIG. 6 this is illustrated schematically as an adjusting interface 609.

The gas-flushed measurement head 602, the flush interface 608 and the adjusting interface 609 are not necessary if only a simple measurement device with one measurement head is required, which is why they are drawn with dashed lines in FIG. 6.

For the purpose of easy and practical use, it is often advantageous to collect as much of the components shown in FIG. 6 into a single hand-held entity. During the development work involved with the invention a roughly pistol-shaped entity has been produced, in which the measurement head 601 (or 602) constitutes a muzzle-and-sight part, and the detection optics unit 603 is located in a handle part.

Figure 7:
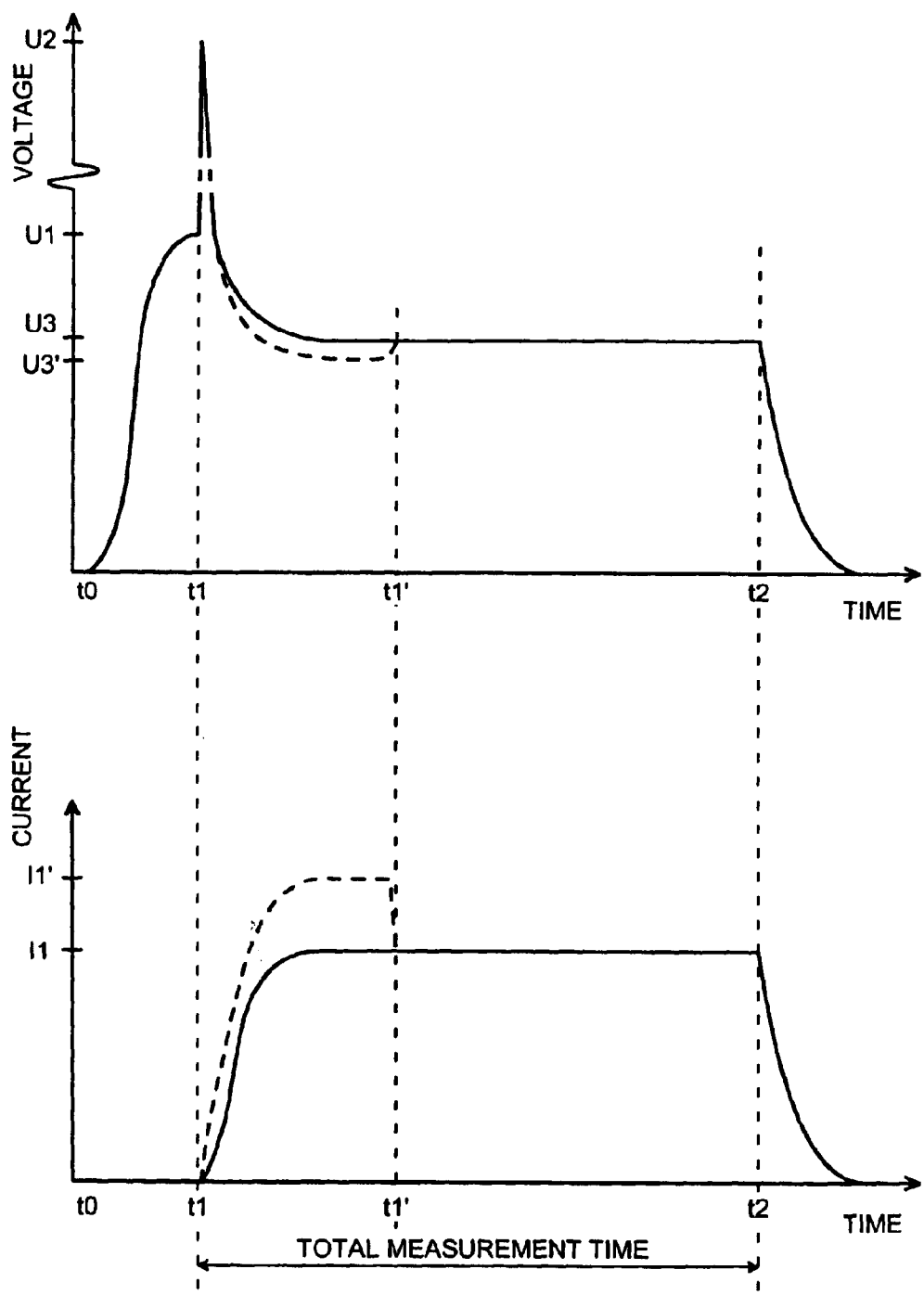

FIG. 7 illustrates schematically an exemplary behaviour of voltage and current between the arc electrode and the material to be measured for the duration of a measurement. At a time t0 there is begun a voltage build-up between the the arc electrode and the material to be measured. When this voltage has reached a predetermined value U1, a sudden high voltage spike is superimposed therewith. This high voltage spike causes an initial discharge, also known as the ignition spark, between the arc electrode and the material to be measured. The moment t1 of applying the high voltage spike is the beginning time for a measurement. During the high voltage spike the voltage reaches a value U2, but very quickly it falls back to the value U1 or even lower. In FIG. 7 we assume that after the high voltage spike at moment t1 the voltage stabilizes at a level U3, where it stays until a later moment t2, after which the voltage is allowed to decay to zero. The time between moments t1 and t2 is the total measurement time.

An electric current between the arc electrode and the material to be measured begins to flow at moment t1. From the initial moment the current value increases until a current limiter in the high voltage source limits it into a value I1, where it stays until cutting off the voltage at moment t2 causes also the current to decay to zero. The coupling between voltage and current values between moments t1 and t2 depends on the structure and control method of the high voltage source: if constant power control is applied, the burn-time voltage U3 is definitely lower than the initial value U1, because the product of voltage and current must remain the same. However, it is possible to apply other kinds of control principles, even constant voltage and constant current control, in which case the voltage would restabilize into the value U1 after spiking into U2 for a very short duration of time.

As an alternative to the above-explained basic measurement it is possible to use so-called pre-burning, which means that from the beginning moment t1 of the measurement time until a later moment t1', which however comes earlier than the end time t2, the current through the arc is allowed to reach a slightly higher value I1'. This is shown as a dashed-line addition to the current curve. Assuming constant power control, allowing a higher current means lowering the voltage value into U3' until the moment t1' after which normal burning at U3 and I1 is resumed.

Typical values are U1≈160 V, 5 kV≦U2≦20 kV, 20 V≦U3≦160 V (typically U3≈50 V), and 1 A≦I1≦10 A. With these values the total measurement time is between 0.5 s and 5 s.

What is claimed is:

1. A measurement device for exciting constituent particles of a material to be measured through the use of an electric arc and for detecting the intensity of optical radiation emitted by excited constituent particles at the moment of relaxation from an excited state, the measurement device comprising:

an arc electrode that comprises a rod part of a certain thickness and has a pointed end having a certain grinding angle, holding means for holding the pointed end of the arc electrode at a certain distance from the material to be measured for the duration of a measurement, a voltage and current supply for generating and maintaining a voltage between the arc electrode and the material to be measured and for supplying current through the arc electrode for the duration of a measurement, and focusing and detection optics for collecting optical radiation from an electric arc between the arc electrode and the material to be measured and for detecting the intensity associated with a certain selected wavelength of the collected optical radiation;

wherein:

the thickness of the rod part in the arc electrode is between 2 and 10 mm, the grinding angle of the pointed end of the arc electrode is between 40 and 130 degrees, the holding means are arranged to keep the pointed end of the arc electrode at a distance between 0.5 and 3 mm from the material to be measured for the duration of a measurement, the voltage and current supply is arranged to supply an ignition spark voltage between 5 and 20 kV, an arc voltage between 20 and 160 V and an arc current between 1 and 10 A, and the focusing and detection optics are arranged to collect and detect optical radiation at least on a wavelength of 193 nm.

2. A measurement device according to claim 1, wherein:

the holding means comprise a tube that has a circular cross section and an open end, so that the edges of said tube at said open end define a plane that is perpendicular to the longitudinal dimension of said tube, the arc electrode is located within said tube coaxially with said tube, and the pointed end of the arc electrode is located at a distance between 0.5 and 3 mm into said tube from said plane defined by said edges of said tube at said open end.

3. A measurement device according to claim 2, wherein a portion of a side wall of said tube is cut out starting from said open end, so that the edges of said cut-out portion define an open window into the tube.

4. A measurement device according to claim 3, wherein:

the focusing optics comprise a lens for collecting optical radiation from an electric arc between the arc electrode and the material to be measured and for directing such collected optical radiation further in the focusing and detection optics, said lens having a certain optical axis, and the measurement device comprises a holder that is arranged to hold said lens outside said tube in a position in which one end of said optical axis extends through said window into a space between the pointed end of the arc electrode and said plane defined by said edges of said tube at said open end.

5. A measurement device according to claim 4, wherein said holder is also arranged to hold an optical fibre in a position in which another end of said optical axis extends into said optical fibre.

6. A measurement device according to claim 5, wherein the length of said optical fibre is less than 60 cm.

7. A measurement device according to claim 5, wherein:

said optical axis extends into one end of said optical fibre, the measurement device comprises a collimator at another end of said optical fibre as well as a slit arranged to separate a beam from optical radiation coming from said collimator, and the measurement device additionally comprises a grating arranged to disperse optical radiation coming from said slit, as well as a location-sensitive detector arranged to receive and detect dispersed light from said grating.

8. A measurement device according to claim 7, comprising a mirror between said grating and said location-sensitive detector.

9. A measurement device according to claim 1, comprising:

a measurement head and a detection optics unit separate from said measurement head, and mechanical attachment means for detachably attaching said measurement head to said detection optics unit; wherein:

said measurement head comprises said arc electrode, said holding means and focusing optics, and said detection optics unit comprises detection optics, and said mechanical attachment means are arranged to align said measurement head and said detection optics unit with each other so that a continuous optical path extends from said measurement head into said detection optics unit.

10. A measurement device according to claim 9, comprising a gastight sealing arrangement between said measurement head and said detection optics unit, and comprising in association with said detection optics unit a flush interface for allowing said detection optics unit to be flushed with a gaseous medium.

11. A measurement device according to claim 10, comprising a valve at the opto-mechanical interface between said measurement head and said detection optics unit, for selectively allowing flushing gaseous medium to flow from said detection optics unit into said measurement head.

12. A method for characterising the composition of a material to be measured, comprising the steps of:

producing an electric arc at a surface of the material to be measured, thus defining an arcing area, allowing the arcing area to be open to ambient air, keeping a current density in the electric arc low enough for excited carbon atoms within the arcing area to emit meaningful numbers of optical radiation quanta on the wavelength of 193.090 nm collecting optical radiation emitted by excited particles within the arcing area, detecting the intensity of collected optical radiation on the wavelength of 193.090 nm and associating the detected intensity with a characteristic of the material to be measured.

13. A method according to claim 12, wherein the step of keeping a current density in the electric arc low enough involves using a thick and blunt arc electrode in order to distribute the electric arc spatially into a large cross section.

14. A method according to claim 12, wherein the step of keeping a current density in the electric arc low enough involves keeping an arc electrode close to a surface of the material to be measured in order to distribute the electric arc spatially into a large cross section.

15. A method according to claim 12, wherein the step of keeping a current density in the electric arc low enough involves limiting the electric current through the electric arc during a measurement.

16. A method according to claim 12, wherein the step of keeping a current density in the electric arc low enough involves limiting the voltage across the electric arc during a measurement.

* * * * *